United States Patent [19]

Bennink

[11] Patent Number: 5,418,228
[45] Date of Patent: May 23, 1995

[54] CONTRACEPTIVE REGIMEN

[75] Inventor: Herman J. T. C. Bennink, Driebergen, Netherlands

[73] Assignee: Akzo N.V., Arnhem, Netherlands

[21] Appl. No.: 182,304

[22] Filed: Jan. 14, 1994

Related U.S. Application Data

[63] Continuation of Ser. No. 53,841, Apr. 27, 1993, abandoned, which is a continuation of Ser. No. 809,724, Dec. 17, 1991, abandoned.

[30] Foreign Application Priority Data

Dec. 17, 1990 [EP] European Pat. Off. ............ 90203372

[51] Int. Cl.$^6$ .............................................. A61K 31/56
[52] U.S. Cl. .................................... 514/182; 514/170; 514/179; 514/843
[58] Field of Search ................. 514/170, 179, 182, 843

[56] References Cited

U.S. PATENT DOCUMENTS 4,530,839 7/1985 Pasquale .............................. 514/171
4,962,098 10/1990 Boissenneault ...................... 514/170

Primary Examiner—Raymond Henley, III
Assistant Examiner—Kimberly R. Jordan
Attorney, Agent, or Firm—Mary E. Gormley; William M. Blackstone

[57] ABSTRACT

A contraceptive method and regimen utilizing an initially greater amount of progestogen, which gradually tapers over the period in which the contraceptive is administered. The regimen includes a multiphasic combination and contraceptive kit containing at least 21 daily sequential dosage units divided into 3 phases. The first phase contains 6–8 dosage units, each containing a progestogen at a dosage equivalent in progestogenic activity to 75–150 μg desogestrel and an estrogen at a dosage equivalent in estrogenic activity to 20–25 μg ethinyl estradiol. The second phase contains 6–8 dosage units, each containing less progestogen than in the previous dosage units, but still having progestogen equivalent to 75–125 μg desogestrel and an estrogen equivalent to 20 μg ethinyl estradiol. The third phase contains 6–8 dosage units, each containing less progestogen than in the previous dosage units, but still containing a progestogen equivalent to 75–100 g desogestrel and an estrogen equivalent to 20 μg ethinyl estradiol. The kit may also include another phase of 4 to 7 dosage units having no contraceptive steroid.

18 Claims, No Drawings

CONTRACEPTIVE REGIMEN

This is a continuation of application Ser. No. 08/053,841 filed Apr. 27, 1993, now abandoned, which is a continuation of application Ser. No. 07/809,724, filed Dec. 17, 1991, now abandoned.

TECHNICAL FIELD

The invention relates generally to contraceptive preparations, and more specifically to an oral contraceptive regimen.

BACKGROUND ART

Known oral contraceptive regimens typically involve administering tablets containing a combination of estrogen and progestogen to an adult female over her menstrual cycle, usually followed by a "pill-free" or blank pill period. The amount of progestogen in the tablets of these regimens typically increases during the administration of the regimen. Alternatively, the amount of progestogen may remain fixed, or reaches a peak and then declines.

For example in French Patent Application No. 2,223,018 to Ortho Pharmaceutical, a progestogen is administered from at least the fifth day to the twenty-fifth day of the menstrual cycle, the dosage of the progestogen being greater during the last seven days of administration than it is during the first seven days.

Another example of an oral contraceptive regimen which increases the amount of progestogen throughout the woman's menstrual cycle is described in European Patent Application No. 36,229 to Akzo, nv.

In Belgian Patent No. 892,801 to Syntex (U.S.A.) Inc., a method of treating menopause is described also involving an increase in the amount of progestogen administered during the regimen's cycle.

German Patent Application No. 3,229,612 to Syntex (U.S.A.) Inc. describes a contraceptive regimen wherein the amount of progestogen administered peaks at mid-cycle, but then decreases.

U.S. Pat. No. 4,292,315 to Vorys describes another contraceptive regimen having a mid-menstrual cycle peak of progestogen and then subsequently declines. In this regimen, during the first 7 days, no exogenous steroids are administered. During days 8 to 14, the tablets administered may contain only a progestogen (e.g. 0.35 milligrams ("mg") of norethindrone). During days 15 to 18, tablets containing both an estrogen and the progestogen (e.g. 0.35 mg of norethindrone) are administered. During days 19 to 25, tablets containing both an estrogen and a progestogen (e.g. 1.0 mg of norethindrone acetate, which is approximately twice as potent as norethindrone) are administered. Finally during days 26 to 28, tablets are administered in which the amount of estrogen and progestogen are at half the daily dosage of the preceding 7 tablets (e.g. 0.35 mg norethindrone).

Canadian Patent Application No. 2,000,438 to Akzo, nv describes a multiphasic oral contraceptive preparation containing a progestogen and an estrogen in a first phase, and a progestogen only in the second phase. The amount of progestogen in the second phase is less than that in the last dosage unit of the first phase. The first phase may be split-up into three sub-phases, each successive sub-phase having more progestogen than the one earlier.

DISCLOSURE OF THE INVENTION

It is found that by initially starting with a high amount of progestogen—after the usual 7 day pill-free or blank period—then gradually tapering the progestogen dosage over the contraceptive regimen, an effective oral contraceptive regimen results having a relatively lower amount of contraceptive steroids.

The invention thus includes a multiphasic combination and contraceptive kit containing from 21 to 24 daily sequential dosage units. The 21 dosage units are divided into three phases. The first phase contains 6 to 8 first dosage units, each containing a progestogen at a dosage equivalent in progestogenic activity to 75 to 150 micrograms ("μg") desogestrel and an estrogen at a dosage equivalent in estrogenic activity to 20-25 μg ethinyl estradiol. The second phase contains 6 to 8, preferably 7, each containing less progestogen than in the first dosage units, but still having progestogen in a dosage equivalent in progestogenic activity to 75 to 125 μg desogestrel and an estrogen at a dosage equivalent in estrogenic activity to 20 μg ethinyl estradiol. The third phase contains 6 to 8 third dosage units, each containing less progestogen than in the earlier dosage units, but still containing a progestogen at a dosage equivalent in progestogenic activity 75 to 100 μg desogestrel and an estrogen at a dosage equivalent in estrogenic activity to 20 μg ethinyl estradiol.

The kit may also include a fourth phase of 4 to 7 fourth dosage units having no contraceptive steroids.

The invention also includes a pharmaceutical product (i.e. the birth control pack containing the dosage unit regimen), and a process of manufacturing this pharmaceutical product.

BEST MODE OF THE INVENTION

Preferred progestogens for use with the invention include 3-ketodesogestrel ("etonogestrel"), desogestrel, levonorgestrel, norgestrel, gestodene, and other compounds with similar progestogenic activity. Especially preferred are 3-ketodesogestrel and desogestrel. As an approximation, levo-norgestrel, desogestrel, and 3-ketodesogestrel are relatively equipotent, when administered orally, in progestogenic activity. Gestodene is approximately 1.5 times as potent as these compounds orally. Norgestrel is about one-half as potent as levonorgestrel.

Each phase preferably contains seven dosage units. In the first dosage units, 125 μg of desogestrel or 3-ketodesogestrel are preferably used. In the second dosage units, 100 μg of desogestrel or 3-keto-desogestrel are preferably used. In the third dosage units, 75 μg of desogestrel or 3-ketodesogestrel are preferably used.

Examples of preferred estrogens include 17β-estradiol and ethinyl estradiol. Mestranol and 17-α-ethinyl estradiol 3-methylether are also useful estrogens. As an approximation and when administered orally, 1 mg of 17β-estradiol is equivalent in estrogenic activity to 0.015 mg of ethinyl estradiol and 0.030 mg of mestranol.

The estrogen and progestogen ("contraceptive steroids"), or either of them are incorporated into dosage units for oral administration. The term "dosage unit" generally refers to physically discrete units suitable as unitary dosages for humans or animals, each containing a predetermined quantity of active material (e.g. estrogen or progestogen) calculated to produce the desired effect.

Conventional techniques may be used to make dosage units according to the invention. Conventional methods and compositions for making such dosage units are well-known to those skilled in the art. For example, methods and compositions for making tablets and pills, containing active ingredients, are described in the standard reference, Chase et al., *Remington's Pharmaceutical Sciences*, (16th ed., Mack Publishing Co., Easton. Pa., U.S.A., 1980) ("*Remington's*"), at pages 1553 through 1584. Methods of making powders, and their composition are described at pages 1535 through 1552 of the reference. Methods of coating pharmaceutical dosage forms are described at pages 1585 to 1593 of *Remington's*.

For making dosage units, e.g. tablets, the use of conventional additives, e.g. fillers, colorants, polymeric binders and the like is contemplated. In general any pharmaceutically acceptable additive which does not interfere with the function of the active compounds can be used in the one or more of the compositions.

Suitable carriers with which the compositions can be administered include lactose, starch, cellulose derivatives and the like used in suitable amounts. Lactose is a preferred carrier. Mixtures of carriers can also be used.

A process of manufacturing the pharmaceutical product according to the invention preferably involves incorporating the desired dosages of contraceptive steroid (i.e. progestogen and estrogen) into a tablet by known techniques. Tablets containing different amounts and types of contraceptive steroids may be of different colors, and kept in different portions of, for example, a blister pack. The package containing the dosage units will preferably contain 21 or 28 dosage units arranged sequentially therein. Preferably there will be 28 dosage units, of which seven will be blanks.

A method of contraception using the invention comprises administering, either enterally or parenterally, to a female of child-bearing age:

a) no contraceptive steroids for the first 7 days;

b) a progestogen at a daily dosage equivalent in progestogenic activity to 75 to 150 μg desogestrel administered orally, and an estrogen at a daily dosage equivalent in estrogenic activity to 20–25 μg ethinyl estradiol administered orally for the next 6 to 8 days;

c) a progestogen at a daily dosage equivalent in progestogenic activity to 75 to 125 μg desogestrel administered orally, but in an amount less than that administered during the prior 6 to 8 days, and an estrogen at a daily dosage equivalent in estrogenic activity to 20 μg ethinyl estradiol administered orally for the next 6 to 8 days; and d) a progestogen at a daily dosage equivalent in progestogenic activity 75 to 100 μg desogestrel administered orally, but in an amount less than that administered during the prior 6 to 8 days, and an estrogen at a daily dosage equivalent in estrogenic activity to 20 μg ethinyl estradiol administered orally for the last 7 days.

A preferred method of contraception using the invention comprises orally administering to a female:

a) for the first 7 days, no dosage units at all;

b) for the next 7 days, first dosage units containing a progestogen at a daily dosage equivalent in progestogenic activity to 75 to 150 μg desogestrel and an estrogen at a dosage equivalent in estrogenic activity to 20–25 μg ethinyl estradiol;

c) for the next 7 days, second dosage units containing less progestogen than in the first dosage units, but still having a progestogen at a daily dosage equivalent in progestogenic activity to 75 to 125 μg desogestrel and an estrogen at a daily dosage equivalent in estrogenic activity to 20 μg ethinyl estradiol; and d) for the last 7 days, third dosage units containing less progestogen than in the second dosage units, but still containing a progestogen at a daily dosage equivalent in progestogenic activity 75 to 100 μg desogestrel and an estrogen at a daily dosage equivalent in estrogenic activity to 20 μg ethinyl estradiol.

After the completion of one cycle of the regimen, the regimen may be repeated for as long as contraception is desired. These methods might also include administering blank dosage units during the first seven days. One or more dosage units may contain an iron salt (e.g. 75 mg of ferrous fumarate) if desired.

This regimen is effective and can be used with a relatively low amount of contraceptive steroids.

The invention is further explained by the following illustrative EXAMPLES.

| Compound | Amount (mg/tablet) |
|---|---|
| Compositions of tablets: | |
| EXAMPLE I | |
| A. In the first phase: (7 tablets) | |
| ethinyl estradiol | 0.020 |
| desogestrel | 0.125 |
| potato starch | 6.500 |
| povidone | 1.950 |
| stearic acid | 0.650 |
| colloidal silicone dioxide | 0.650 |
| dl-α-tocopherol | 0.080 |
| lactose            qsad | 65.000 |
| B. In the second phase: (7 tablets) | |
| ethinyl estradiol | 0.020 |
| desogestrel | 0.100 |
| potato starch | 6.500 |
| povidone | 1.950 |
| stearic acid | 0.650 |
| colloidal silicone dioxide | 0.650 |
| dl-α-tocopherol | 0.080 |
| lactose            qsad | 65.000 |
| C. In the third phase: (7 tablets) | |
| ethinyl estradiol | 0.020 |
| desogestrel | 0.075 |
| potato starch | 6.500 |
| povidone | 1.950 |
| stearic acid | 0.650 |
| colloidal silicone dioxide | 0.650 |
| dl-Δ-tocopherol | 0.080 |
| lactose            qsad | 65.000 |
| D. In the fourth phase: (7 tablets) | |
| potato starch | 6.500 |
| povidone | 1.950 |
| stearic acid | 0.650 |
| colloidal silicone dioxide | 0.650 |
| dl-α-tocopherol | 0.080 |
| lactose            qsad | 65.000 |
| EXAMPLE II | |
| A. In the first phase: (7 tablets) | |
| ethinyl estradiol | 0.020 |
| 3-ketodesogestrel | 0.125 |
| potato starch | 6.500 |
| povidone | 1.950 |
| stearic acid | 0.650 |
| colloidal silicone dioxide | 0.650 |
| dl-α-tocopherol | 0.080 |
| lactose            qsad | 65.000 |
| B. In the second phase: (7 tablets) | |
| ethinyl estradiol | 0.020 |

-continued

| Compositions of tablets: | |
|---|---|
| Compound | Amount (mg/tablet) |
| 3-ketodesogestrel | 0.100 |
| potato starch | 6.500 |
| povidone | 1.950 |
| stearic acid | 0.650 |
| colloidal silicone dioxide | 0.650 |
| dl-α-tocopherol | 0.080 |
| lactose          qsad | 65.000 |
| C. In the third phase: (7 tablets) | |
| ethinyl estradiol | 0.020 |
| 3-ketodesogestrel | 0.075 |
| potato starch | 6.500 |
| povidone | 1.950 |
| stearic acid | 0.650 |
| colloidal silicone dioxide | 0.650 |
| dl-α-tocopherol | 0.080 |
| lactose          qsad | 65.000 |
| D. In the fourth phase: Same as EXAMPLE I.D. | |
| EXAMPLE III | |
| A. In the first phase: (7 tablets) | |
| micronized(17β)estradiol | 2.000 |
| desogestrel | 0.125 |
| potato starch | 6.500 |
| povidone | 1.950 |
| stearic acid | 0.650 |
| colloidal silicone dioxide | 0.650 |
| dl-α-tocopherol | 0.080 |
| lactose          qsad | 65.000 |
| B. In the second phase: (7 tablets) | |
| micronized estradiol | 2.000 |
| desogestrel | 0.100 |
| potato starch | 6.500 |
| povidone | 1.950 |
| stearic acid | 0.650 |
| colloidal silicone dioxide | 0.650 |
| dl-α-tocopherol | 0.080 |
| lactose          qsad | 65.000 |
| C. In the third phase: (7 tablets) | |
| micronized estradiol | 2.000 |
| desogestrel | 0.075 |
| potato starch | 6.500 |
| povidone | 1.950 |
| stearic acid | 0.650 |
| colloidal silicone dioxide | 0.650 |
| dl-α-tocopherol | 0.080 |
| lactose          qsad | 65.000 |
| D. In the fourth phase: Same as EXAMPLE I.D. | |
| EXAMPLE IV | |
| A. In the first phase: (8 tablets) | |
| ethinyl estradiol | 0.025 |
| desogestrel | 0.150 |
| potato starch | 6.500 |
| povidone | 1.950 |
| stearic acid | 0.650 |
| colloidal silicone dioxide | 0.650 |
| dl-α-tocopherol | 0.080 |
| lactose          qsad | 65.000 |
| B. In the second phase: (8 tablets) | |
| ethinyl estradiol | 0.020 |
| desogestrel | 0.125 |
| potato starch | 6.500 |
| povidone | 1.950 |
| stearic acid | 0.650 |
| colloidal silicone dioxide | 0.650 |
| dl-α-tocopherol | 0.080 |
| lactose          qsad | 65.000 |
| C. In the third phase: (8 tablets) | |
| ethinyl estradiol | 0.020 |
| desogestrel | 0.100 |
| potato starch | 6.500 |
| povidone | 1.950 |
| stearic acid | 0.650 |
| colloidal silicone dioxide | 0.650 |
| dl-α-tocopherol | 0.080 |
| lactose          qsad | 65.000 |
| D. In the fourth phase: Same as EXAMPLE I.D. | |

Reference herein to specific embodiments or examples should not be interpreted as limitations to the scope of the invention, which is defined by the appended claims.

What is claimed is:

1. A pharmaceutical product comprising a package containing 21 to 24 daily sequential dosage units of:
   a first phase of 6 to 8 first dosage units, said first dosage units each containing a progestogen at a dosage equivalent in progestogenic activity to 75 to 150 micrograms desogestrel and an estrogen at a dosage equivalent in estrogenic activity to 20 to 25 micrograms ethinyl estradiol;
   a second phase of 6 to 8 second dosage units, said second dosage units each containing less progestogen than in the first dosage units, but still having a progestogen at a dosage equivalent in progestogenic activity to 75 to 125 micrograms desogestrel and an estrogen at a dosage equivalent in estrogenic activity to 20 micrograms ethinyl estradiol; and
   a third phase of 6 to 8 third dosage units, said third dosage units each containing less progestogen than in the second dosage units, but still containing a progestogen at a dosage equivalent in progestogenic activity to 75 to 100 micrograms desogestrel and an estrogen at a dosage equivalent in estrogenic activity to 20 micrograms ethinyl estradiol.

2. The pharmaceutical product of claim 1 wherein the kit further comprises a fourth phase of 4 to 7 fourth dosage units containing no contraceptive steroids.

3. The pharmaceutical product of claim 1 or claim 2 wherein said progestogen is selected from the group consisting of 3-ketodesogestrel, desogestrel, levonorgestrel, gestodene, and mixtures thereof.

4. The pharmaceutical product of claim 3 wherein the progestogen in all phases containing a progestogen is desogestrel or 3-ketodesogestrel.

5. The pharmaceutical product of claim 1, wherein said estrogen is selected from the group consisting of 17β-estradiol, ethinyl estradiol, mestranol, 17-α-ethinyl estradiol 3-methylether, and mixtures thereof.

6. The pharmaceutical product of claim 5 wherein the estrogen administered in all phases containing an estrogen is 17β-estradiol or ethinyl estradiol.

7. A pharmaceutical product comprising a package containing 24 daily sequential dosage units of:
   a first phase of 8 first dosage units, each containing a progestogen at a dosage equivalent in progestogenic activity to 150 μg desogestrel and an estrogen at a dosage equivalent in estrogenic activity to 25 μg ethinyl estradiol;
   a second phase of 8 second dosage units, each containing a progestogen at a dosage equivalent in progestogenic activity to 125 μg desogestrel and an estrogen at a dosage equivalent in estrogenic activity to 20 μg ethinyl estradiol; and
   a third phase of 8 third dosage units, each containing a progestogen at a dosage equivalent in progestogenic activity to 100 μg desogestrel and an estrogen at a dosage equivalent in estrogenic activity to 20 μg ethinyl estradiol.

8. A pharmaceutical product containing sequential phases of dosage units having progestogen and estrogen characterized in that the amount of progestogen contained in the dosage units of each phase of the pharmaceutical product decreases incrementally along with the phase.

9. The pharmaceutical product of claim 2, wherein said progestogen is selected from the group consisting of 3-ketodesogestrel, desogestrel, levo-norgestrel, gestodene, and mixtures thereof.

10. The pharmaceutical product of claim 9, wherein the progestogen in all phases containing a progestogen is desogestrel or 3-ketodesogestrel.

11. The pharmaceutical product of claim 2, wherein said estrogen is selected from the group consisting of 17β-estradiol, ethinyl estradiol, mestranol, 17-α-ethinyl estradiol 3-methylether, and mixtures thereof.

12. The pharmaceutical product of claim 3, wherein said estrogen is selected from the group consisting of 17β-estradiol, ethinyl estradiol, mestranol, 17-α-ethinyl estradiol 3-methylether, and mixtures thereof.

13. The pharmaceutical product of claim 4, wherein said estrogen is selected from the group consisting of 17β-estradiol, ethinyl estradiol, mestranol, 17-α-ethinyl estradiol 3-methylether, and mixtures thereof.

14. The pharmaceutical product of claim 11, wherein the estrogen administered in all phases containing an estrogen is 17β-estradiol or ethinyl estradiol.

15. The pharmaceutical product of claim 12, wherein the estrogen administered in all phases containing an estrogen is 17β-estradiol or ethinyl estradiol.

16. The pharmaceutical product of claim 13, wherein the estrogen administered in all phases containing an estrogen is 17-estradiol or ethinyl estradiol.

17. The pharmaceutical product of claim 6, wherein the estrogen administered in all phases containing an estrogen is ethinyl estradiol.

18. A method of contraception comprising: administering to a female of child-bearing age, for so long as contraception is desired:
   a) no contraceptive steroids for the first 4 to 7 days;
   b) a progestogen at a daily dosage equivalent in progestogenic activity to 77 to 150 μg desogestrel administered orally, and an estrogen at a daily dosage equivalent in estrogenic activity to 20-25 μg ethinyl estradiol administered orally for the next 6 to 8 days;
   c) a progestogen at a daily dosage equivalent in progestogenic activity to 76 to 125 μg desogestrel administered orally, but in an amount less than that administered during the prior 6 to 8 days, and an estrogen at a daily dosage equivalent in estrogenic activity to 20 μg ethinyl estradiol administered orally for the next 6 to 8 days; and
   d) a progestogen at a daily dosage equivalent in progestogenic activity 75 to 100 μg desogestrel administered orally, but in an amount less than that administered during the prior 6 to 8 days, and an estrogen at a daily dosage equivalent in estrogenic activity to 20 μg ethinyl estradiol administered orally for the last 6 to 8 days.

* * * * *

UNITED STATES PATENT AND TRADEMARK OFFICE
CERTIFICATE OF CORRECTION

PATENT NO. : 5,418,228
DATED : May 23, 1995
INVENTOR(S) : Herman J.T.C. Bennink

It is certified that error appears in the above-indentified patent and that said Letters Patent is hereby corrected as shown below:

Column 6, claim 2, line 2, by deleting "kit" and replacing with -- pharmaceutical product --.

Signed and Sealed this

Twenty-ninth Day of August, 1995

Attest:

BRUCE LEHMAN

*Attesting Officer*      *Commissioner of Patents and Trademarks*